United States Patent [19]

Nigam et al.

[11] Patent Number: 5,625,044

[45] Date of Patent: Apr. 29, 1997

[54] METHODS FOR THE PREPARATION OF PURE HOMOLOGOUS SERIES OF MONO TO TETRA FATTY ACYL ESTERS OF SUGARS AND PHARMACEUTICAL FORMULATIONS USEFUL IN THE TREATMENT OF CANCER

[75] Inventors: Vijai N. Nigam, North Hatley; Prométéo Madarnas; Gilles Dupuis, both of Sherbrooke, all of Canada

[73] Assignee: Goudreau Gage Dubec & Martineau, Montreal

[21] Appl. No.: 358,188

[22] Filed: Dec. 16, 1994

[51] Int. Cl.$^6$ ............................. C07H 15/06; C07G 3/00
[52] U.S. Cl. .................. 536/18.2; 536/18.5; 536/18.6; 536/115; 536/123
[58] Field of Search ........................... 536/18.6, 18.2, 536/18.5, 115, 123

[56] References Cited

FOREIGN PATENT DOCUMENTS 1120399  3/1982  Canada .

OTHER PUBLICATIONS

Abstract, JP 61–068497, issued Apr. 8, 1986, to Wakabayashi Toshio et al., entitled "Sugaralcohol Ester Derivative and Neutrophils Activator Containing Same", from Patent Abstracts of Japan.

O. Benrezzak et al., "Modulation of Protein Kinase C Activity by Palmitoyl Esters of Maltose", *Cancer Biochem. Biophys.*, 13, 13–22 (1992).

O. Benrezzak et al., "Effect of Maltose Tetrapalmitate on Tumor Vascularization and Tumor Growth", *Anticancer Research*, 9, 1815–1818 (1989).

O. Benzerrak et al., "Evaluation of Cortisone–Heparin and Cortisone–Maltose Tetrapalmitate Therapies Against Rodent Tumors. I. Biological Studies", *Anticancer Research*, 2, 1883–1888 (1989).

Benrezzak, O. et al. (1989) Anticancer Research. 9: 1883–1887.

Chen et al. (1973). J. Infect. Dis. 128: S43–S51.

Nishikawa, Y. et al. (1981). Chem. Pharm. Bull. 29 (2): 505–513.

Spiro, R.G. (1966). *Methods in Enzymology* 8 pp. 3–52.

*Primary Examiner*—Nathan M. Nutter
*Attorney, Agent, or Firm*—Schwegman, Lundberg, Woessner & Kluth, P.A.

[57] ABSTRACT

The present invention relates to a method for the making pure homologous series of fatty acyl esters of sugars. The production mono- to tetrapalmitates of maltose is particularly exemplified. Specific compositions containing di-, tri- and tetrapalmitates of maltose show an antitumoral activity, an immunostimulating and, to some extent, an antiangiogenic effects are also described and claimed. They can be used alone or in the presence of angiostatic steroids for treating angiogenesis-dependent deseases. The characterization of one such new compound, maltose 1, 6, 6' tripalmitate which is the active component of this series is included.

26 Claims, No Drawings

METHODS FOR THE PREPARATION OF PURE HOMOLOGOUS SERIES OF MONO TO TETRA FATTY ACYL ESTERS OF SUGARS AND PHARMACEUTICAL FORMULATIONS USEFUL IN THE TREATMENT OF CANCER

Methods for the preparation of pure homologous series of mono to tetra fatty acyl esters of sugars; characterization of one antitumor component as maltose 1, 6, 6' tripalmitate; and pharmaceutical formulations useful in the treatment of cancer.

BACKGROUND OF THE INVENTION

In 1982, a Canadian patent No. 1,120,399 entitled "Pharmaceutical composition for treatment of tumor cells" by Nigam, Vijai N. and Brailovsky, Carlos, A. was granted to Université de Sherbrooke. It described the administration of certain fatty acid esters of mono and disaccharides which surprisingly elicit an antitumor response as shown by an enhancement of the host capacity to reject a large number of tumor cells, to retard growth in tumor size and to induce hemorrhagic tumor necrosis. Fatty acid esters of maltose, galactose, glucose, mannose, arabinose, cellobiose and lactose were particularly useful when the fatty acid comprised 12 to 18 carbon atoms.

At that time the method employed for the preparation of these compounds was not patented since it consisted in a conventional methodology without regards to providing stringent purity requirement and optimal yields. The method that was based on the deployment of a known solvent system used for thin layer chromatography (TLC) on silica gel G plates. It employed a silica gel column instead of silica gel plates, thereby avoiding scraping of bands from plates, and obtained larger amounts of the product. A fraction isolated from the column that gave a thick band of Rf 0.68 on TLC plates and a ratio of glucose to palmitic acid of approximately 0.5 was referred to as maltose tetrapalmitate. The compound prepared accordingly was used for numerous biological experiments.

It was further surprisingly noted that the fraction referred to as maltose tetrapalmitate and used in biological investigation was indeed not pure and, upon rechromatography on TLC plates in other solvent systems, provided 2-3 bands.

In addition, it was further noted that the band of Rf 0.68 in $CHCl_3$: $MeOH$:$H_2O$ (60:25:4) solvent system, upon scraping from unstained silica gel plates could be split into 3 bands upon rechromatography in other solvent systems as well. In addition, it contained small amounts of palmitic acid. These results which came as a surprise established that there may be an association between the three components due to hydrophobic interaction because of the presence of water in the solvent system which was comprised of $CHCl_3$:$MeOH$:$H_2O$, 60:25:4. To our satisfaction, the property of hydrophobic interactions between various bacterial lipid As (which are structurally similar to maltose palmitates) and the splitting of single bands upon rechromatography had been described before (Chen et al. J. Infect. Dis. 128: 543-551, 1973).

The question confronting us was to find the identity of the three components and to find out the most active antitumor component among them, characterize it, and to see if associating them in various ratios provided a more active product than individual components as far as its antitumoral activity in vivo and its solubility in aqueous solvent were concerned. To date, we have seen no report for the isolation of pure fractions of maltose palmitates which have been structurally well characterized and have been tested for their antitumor activity. One report based on our initial finding described antitumor activity of maltose mono fatty acyl esters which was superior to maltose poly fatty acyl esters but the components were not well characterized and the purification procedure used was column chromatography similar to the one used by us (Nishikawa, Y., Yoshimoto, K., Nishijima, M., Fukuoka, F. and Ikekawa, T. Chem. Pharm. Bull. 29 (2): 505-513, 1981). Mono esters are mild detergents and could lyse tumor cells at the high concentrations used by those researchers.

Another remarkable finding made by us (Anticancer Res. 9:1883-1888, 1989) was that a combination of crude MTP with cortisone or $\alpha$-OH progesterone or tetrahydro S resulted in a high antitumor activity and it was interpreted as being caused by the antiangiogenic activity of the combination, rather than immune stimulating activity, since hydrocortisone is known to be highly immunosuppressive.

It should be noted that both the Health Protection Branch (HPB) in Canada and FDA in U.S.A. insist on the use of characterized products for human use, especially when they are prepared by synthetic routes. The use of uncharacterized mixtures alone or in formulations is not permitted. The major problem in the use of uncharacterized partially purified mixtures of substances is badge variation and the presence of impurities that may remain associated within the mixture and elicit toxic reactions on dose escalation and upon chronic use. In our case, once it became apparent that our column prepared MTP (as described in our previous patent) was not a single component, there was no excuse for not identifying and characterizing the individual components and finding which was the active one. Indeed, as detailed later, it became clear that the most active component was maltose tripalmitate, rather than maltose tetrapalmitate (as previously thought) and that maltose tetrapalmitate could not even be administered due to its lack of solubility. Maltose tetrapalmitate when emulsified could be injected intraperitoneally (ip) and its activity was derived from its transformation to the maltose tripalmitate. Thus the claim in our earlier patent stating that the active component was maltose tetrapalmitate was only partly true.

It seemed to us that:

1) new methods of purification must be devised using HPLC, which would have a high capacity of resolution and which can be adapted for future large scale isolation of the components, especially with the new pilot plant HPLC separation equipment provided by Waters Inc.;

2) the activities of purified components, individual maltose palmitates, should be tested in the presence and absence of hydrocortisone to see if their activity is based on immunological stimulation, or based on antiangiogenic activity;

3) the active antitumor agents should be structurally characterized after their separation on HPLC using chemical means; and 4) a pharmaceutical formulation should be made to take into account the distribution of individual maltose palmitates in various organs, the rate of degradation of higher palmitate esters into lower palmitate esters, and a good solubility or dispersibility. This would lead to suggested optimum dose and/or delivery rate devised specifically for cancers of different organs.

The isolation of the three individual products contained in the previously described MTP was attained in a long and painstaking manner. The use of HPLC as a chromatographic tool for separation of closely related substances is well known and the resolving power of HPLC surpasses those of other chromatographic techniques. However, finding the appropriate support systems and solvents requires numerous trials to arrive at the most suitable combinations. Up to date, to our knowledge, fatty acyl esters of sugar have not been subjected to rigorous separation and few, if any, have been structurally characterized with respect to the position of esterification. Most characterizations end up solely with the number of fatty acid residue per mono or disaccharide molecule.

STATEMENT OF THE INVENTION

The systems developed by us for the separation of mixtures of fatty acyl maltose are unique insofar they define a specific scheme used in their separation. First, the dimethyl formamide use as a solvent has been eliminated in Method 3 which also provides maximum maltose tripalmitate yield. The mono acylated product is isolated by solvent fractionation and only the di, tri and tetra acylated components require the use of HPLC The solvent systems hereinbelow described for HPLC separation provide the most effective method of separation of these three components.

The possibility that new commercially feasible solvent systems can be developed in the future for the separation of fatty di, tri and tetra acyl disaccharides by HPLC is remote since (i) the new solvents will be of higher molecular weight and higher boiling point since we have already tried low molecular weight low boiling point solvents acceptable to HPB, Canada, (ii) they will not be cost effective with respect to availability, price and their removal from isolated fatty acyl esters, (iii) their toxic nature could be a barrier if traces remain associated with the purified fatty acyl esters and, (iv) they have to be those which are approved by HPB for use in drug purification.

DESCRIPTION OF THE INVENTION

The present invention is hereinbelow described in the following Figures and specific embodiments, which purpose is to illustrate this invention rather than to limit its scope.

METHOD 1

Improved and commercially applicable methods of preparation of maltose palmitates.

Ten millimole (10 mmole) dry maltose (dried by trituration of commercial maltose hydrate with distilled pyridine and evaporation of pyridine under reduced pressure) was added to 40 ml distilled dimethyl formamide (DMF) followed by 4 ml of distilled pyridine. Forty millimole (40 mmole) palmitoyl chloride (Aldrich Chem. Co.) was added to the solution dropwise with stirring. The reaction was allowed to proceed overnight (14–16 h) with stirring at 60° C. in the hood. Fifty ml toluene was added to the reaction flask and the mixture was then rotary evaporated at 60° C. which resulted in an azeotropic removal of excess pyridine and DMF. This step was repeated with two (2) more 50 ml portions of toluene. The crude reaction product (16.5 g) was dissolved in 75 ml chloroform, followed by the addition of 50 g 70–230 mesh silica gel (Merck). The mixture was rotary evaporated at 40° C. to affect suspension of the crude product on the solid silica base. The suspended product was placed in a Buchner funnel and washed with 4 liters of warm (30° C.) distilled water. This step was required to remove pyridine hydrochloride (4 g) which was a reaction product, free maltose (only minute amounts were found), maltose mono palmitates, any remaining DMF and pyridine and to convert any free palmitoyl chloride to palmitic acid. The suspended product was then rotary evaporated at 40° C. to remove water, placed in a Buchner funnel and washed with chloroform to remove palmitic acid (recovery 4.5 g), followed by elution of the product (maltose palmitates referred to as glycolipids) with chloroform: methanol (1:1). The dissolved product was filtered through a glass fiber filter to remove particles of silica gel and rotary evaporated to dryness followed by vacuum desiccation (48 h). Final traces of impurities were removed by dissolving the product in hot (60° C.) ethanol and cooling to 0° C., which resulted in the precipitation of the product. The product (glycolipid mixture of di, tri and tetra palmitates of maltose) was recovered by suction filtration. This step was repeated once more. The recovery was 7 g. The product gave 4 to 5 bands on TLC using chloroform: methanol (9: 1) as the developing solvent.

Separation of glycolipids into groups of di, tri and tetra palmitoyl maltose by flash chromatography.

A 5 cm i.d.×45 cm glass column fitted with an air flow adapter was packed with 20 cm of dry silica gel G (Merck 0.040–0.063 mm). Five mm of washed sand was placed on top of the bed followed by 400 ml of chloroform ($CHCl_3$). Using an air pressure of 10 psi, the $CHCl_3$ was washed through the bed thus packing and equilibrating the column. Five (5.0) gm maltose palmitate mixture prepared as described above was dissolved in 10 ml of chloroform and the dissolved sample was pushed into the top of the bed. Fractions were eluted using 400 ml of each of the following solvents in order of increasing polarity except for the first solvent which was 600 ml: (1) $CHCl_3$; (2) $CHCl_3$:MeOH, (99:1); (3) $CHCl_3$: MeOH, 97:3; (4) $CHCl_3$: MeOH, 93:7; (5) $CHCl_3$: MeOH, 85:15; (6) $CHCl_3$: MeOH, 65:35; and (7) $CHCl_3$: MeOH, 50:50. The volume of each fraction was 30 ml and the number of fractions collected was 92. The fractions were spotted on 20×20 cm glass supported silica gel 60 plates (0.25 mm layer—E. Merck) plate. Fractions 1–23 were developed in $CHCl_3$: MeOH (99:1), fractions 24–46 in $CHCl_3$: MeOH (98:1) and fractions 47–92 in $CHCl_3$: MeOH (90:10). Following development, the plates were dried and sprayed with a solution of 0,025 M ceric sulfate and 0.02 M ammonium molybdate in 10% $H_2SO_4$, followed by heating the plates at 100° C. for 5 min in an oven. The spray reagent reacted with maltose palmitates to give a blue color when heated. Fractions with identical Rf values were combined, and the combined fractions were analysed on TLC alongside individually purified bands of determined palmitic acid/maltose ratios. They were obtained upon scraping of single bands and running in 2-solvents till no split of bands occurred. The fractions were recrystallized in 95% ethanol, suction filtered and then dried in a vacuum desiccator. The distribution of palmitate was as described in Table 1.

Preparation of maltose tetra and tripalmitate mixture from crude maltose palmitates 5 g maltose palmitates was applied to a flash chromatography column as described above. The hexa and penta palmitates of maltose were eluted with 300 ml $CHCl_3$, followed by eluting tetra and tri palmitates with 400 ml $CHCl_3$: MeOH (97:3), The di and mono palmitates were eluted with 400 ml $CHCl_3$: MeOH (50:50), The column was made ready for another purification by reequilibrating with 400 ml $CHCl_3$. The fractions were filtered through a glass fiber filter and the products and solvents were recovered by rotary evaporation. The mixture of maltose tetra and tripalmitates was then subjected to purification by HPLC as described below,

TABLE 1

Flash chromatography of maltose palmitates (for details see text) The fractions were combined on the basis of their composition when chromatographed on TLC. Sample applied was 5.5 g (NMR ratio 2.3)

| Number of tubes combined | Fraction No. | Eluting solvent(s) and their volume | Weight of product recovered (mg) | % yield | Palmitate maltose ratio by NMR | Interpretation |
|---|---|---|---|---|---|---|
| 1–32 | 1 | $CHCl_3$, (600 ml) $CHCl_3$:MeOH (99:1) (270 ml) | 211 | (3.83) | 4.2 | Mostly tetra + little hexa-penta |
| 33–41 | 2 | $CHCl_3$:MeOH (99:1) 130 ml + $CHCl_3$:MeOH (97:3) – 150 ml | 565 | (10.27) | 3.6 | Tetra + Tri |
| 42–43 | 3 | $CHCl_3$:MeOH (97:3) (60 ml) | 306 | 5.57 | 3.4 | Tetra + Tri |
| 44–49 | 4 | $CHCl_3$:MeOH (97:3) (190 ml) | 495 | 8.98 | 2.8 | Tri + Di |
| 50–52 | 5 | $CHCl_3$:MeOH (97:3) (90 ml) | 449 | 8.16 | 2.5 | Tri + Di |
| 53–56 | 6 | $CHCl_3$:MeOH (97:3) (120 ml) | 1376 | 25.03 | 2.3 | Di + Tri |
| 57–60 | 7 | $CHCl_3$:MeOH (97:3) (120 ml) | 437 | 8.86 | 2.2 | Di + Tri |
| 61–69 | 8 | $CHCl_3$:MeOH (97:3) (70 ml) $CHCl_3$:MeOH (85:15) (210 ml) | 554 | 10.08 | 1.8 | Di + Mono |
| 70–75 | 9 | $CHCl_3$:MeOH (85:15) (210 ml) | 597 | 10.86 | 1.5 | Di + Mono |
| 76–77 | 10 | $CHCl_3$:MeOH (85:15) | 114 | –2.07 | — | |
| 78–79 | 11 | $CHCl_3$:MeOH (85:15) | 290 | –5.27 | 1.3 | Di + Mono |
| 80–82 | 12 | Wash $CHCl_3$:MeOH (1:1) | 330 | 6.0 | — | |
| TOTAL | | | 5724 | 104 | | |

Isolation of MTP by high performance liquid chromatography (HPLC)

One hundred mg of mixed fraction No. 2 (tubes 33–41) giving a palmitate maltose ratio of 3.6 (Table I) was subjected to HPLC. The equipment used was a Waters model 6000A solvent delivery system. The column was a stainless steel 0.5 cm×25 cm column packed with 5μ silica supplied by YMC Inc., Morris Plains, N.J., U.S.A. The detector used was a Varian model RI-3 refractive index detector. The column was washed and equilibrated with chloroform methanol (99.5:0.5) and the flow rate was adjusted to 4.0 mVmin. Fractions were collected in tubes at the top of the peaks and at the drop in the peak or appearance of a shoulder. This allowed pure as well as mixed fraction (of two components) to be recovered. Thus 6–7 fractions were collected up to 11.5 min. The next was the predominant fraction which had a peak at 14.5 min (FIG. 1). All the fractions were evaporated and weighed. The major fraction (peak at 14.5 min) was 70 mg providing a yield of 70%. It gave a single band on TLC as shown in FIG. 2. On NMR analysis the product gave a palmitate maltose ratio of 3.7 (NMR determinations are usually underestimates of fatty acid protons) allowing it to be designated MTP. The overall yield of MTP can be regarded as 7 percent of the crude mixed maltose palmitates. This yield can be increased to about 10 percent if fractions at the shoulder of MTP peak are combined and then resubjected to HPLC.

METHOD 2

The individual steps are described below in greater detail.

Step 1. Dehydration of maltose and storage of the anhydrous maltose

Maltose monohydrate (Fisher M-75, Montréal, Qué.) is transformed into its anhydrous form by triturating 500 g lots of maltose monohydrate with 100 ml of freshly distilled pyridine (Fisher Scientific, Montréal, Qué.). The suspension is subjected to evaporation under reduced pressure in a rotary evaporator at 40° C. bath temperature. This procedure results in the azeotropic removal of the water of crystallization along with the pyridine into the distillate. The resulting dry maltose powder can then be stored in a vacuum desiccator over drierite at room temperature for lengthy periods (>2 years).

Step 2. Preparation of maltose palmitates

Anhydrous maltose (100 g=293 mmol) is added to a 2-l round bottomed flask and 750 ml of distilled dimethyl formamide (Anachemia, Montréal, Qué.) is gently poured into the flask followed by the addition of 250 ml of distilled pyridine. The contents are kept over a heating pad at 60° C. to affect dissolution of maltose. A 400 ml separatory funnel is then adjusted over the flask and to it is added 250 g (250/1.45=1712 ml) of a mixture of palmitoyl chloride (Aldrich P. 78) and 100 ml of distilled dimethyl formamide. The palmitoyl chloride is released drop by drop and the contents stirred by holding the flask over a magnetic stirring device, during a period of 30 min–1 hr. A fluffy precipitate that forms is allowed to dissolve before allowing additional amounts of palmitoyl chloride into the reaction mixture. When all the palmitoyl chloride has been added to the flask it is transferred to the heating pad and the rheostat adjusted so that the temperature is raised to 60° C. The flask is then shifted to an oven maintained at 60° C. It is kept there for 18 h. After standing at 60° C. for 18 h, the contents are brought to room temperature and gently added to ice-water mixture (2000 ml) in a 4-l beaker. A large amount of precipitate is formed. The contents are then transferred to a freezer at –20° C. After 2 hours, the solids are filtered over a cooled Bucher funnel and the material is copiously washed with cold distilled water. The solid retained over the Buchner funnel is allowed to dry and stored at 4° C. in a desiccator. The yield of the solids varies from 325 to 350 g. Analysis of the crude maltose palmitates reveals at least 15 bands on TLC. The crude maltose palmitates are stable and give the same profile on HPLC for at least 9 months, a period during which we compared its stability.

Step 3. Pre-HPLC fractionation of crude maltose palmitates

Crude maltose palmitates contain a mixture of palmitates ranging from maltose octa to mono palmitate as well as traces of dimethyl formamide (DMF) and pyridine. The maltose tetra, tri and di palmitates required for the drug formulation are isolated from the crude maltose palmitates by a three-step process.

In the first step, 300 g are extracted with 1000 ml of hot (60° C.) methanol in which maltose octa to penta palmitates are insoluble and are thereby eliminated. In the second step, the hot methanol extract is cooled to 0° C. which results in the precipitation of maltose tetra to mono palmitates, while DMF, pyridine and any other methanol soluble impurities remain in solution. The precipitate is filtered and then dried by vacuum desiccation. In the third step, the precipitate is extracted with heptane:ethanol (95:5) in which maltose mono palmitate is insoluble. The extract is filtered and solvents are removed from the filtrate by rotary evaporation. The recovered product weighs about 100 g (33%) and contains approximately 95% of the maltose tetra, tri and di palmitates present in the crude reaction product, and which are present in the ratio 50:35:15 based on HPLC integration data.

Step 4. Purification of maltose di, tri and tetrapalmitates by HPLC

A PREP LC 3000 80-ml P/N WAT088656 HPLC system with a M59OEEF advanced solvent delivery system (P/N WAT089302), a fraction collector (P/N WAT007441), a M1000 PREP PAK module (P/N WAT089592) and a variable UV detector (P/NWAT098293) and Prepak Silica Cartridge and Column (P/N WAT020732) constitute an entire HPLC purification system for separating maltose palmitates on a semi pilot plant scale. This equipment can load 5 g of the mixture and separate it into its individual components in less than 30 minutes and therefore can process 80 g of maltose palmitates per day.

However, for dealing with small quantities of the material a 10 ml/min delivery system is currently used for providing MTP formulation for animal experiments. The procedure for purifications, which is now standardized is as follows:

Materials: The High Performance Liquid Chromatography System used consists of:

1 System controller (Waters)
1 Data module (Waters)
2 Model 6000 pumps (Waters)
1 U6K Sample injector (Waters)
1 Fixed Wavelength W detector (Waters)
1 10 mm×250 mm normal phase HPLC column (YMC A-023 Sil)
1 3.9 mm×150 mm reverse phase HPLC column (Waters Resolve C-18)

Solvents used are: n-Heptane HPLC (Baker)
Absolute Ethanol
Methanol Accusolu (Anachemia)

Partly purified maltose palmitates were extracted with heptane: ethanol (95:5) and the concentration of the extract was adjusted to 40 mg/ml.

The HPLC system was programmed to deliver the linear gradients shown in FIG. 4 at a flow rate, of 2 ml/min.

The gradient is described below in the form of a table.

| Time (Minutes) | % Heptane | % Ethanol |
| --- | --- | --- |
| 0 | 95 | 5 |
| 22 | 93 | 7 |
| 30 | 85 | 15 |
| 38 | 50 | 50 |
| 39 | 95 | 5 |

A sample of 10 mg crude maltose palmitates (250 µl heptane: ethanol extract) was applied to the system which employed the use of semipreparative silica gel column (described above), and fractions of the major components were collected manually. The palmitate/maltose ratio of the fractions was determined by NMR analysis as shown in the following table:

| Fraction | Elution time (Minutes) of components | Palmitoyl residues/maltose unit |
| --- | --- | --- |
| 1 | 25.51 and 26.77 | 4 |
| 2 | 38.11 | 3 |
| 3 | 42.59 | 2 |

On the basis of the palmitate/maltose ratio fractions 1, 2 and 3 were termed maltose tetrapalmitate, maltose tripalmitate and maltose dipalmitate respectively. However, since the components of fraction 1 were only partially resolved by this technique further purification of this fraction by reverse phase chromatography was performed.

Reverse phase chromatography of fraction 1 was performed using methanol as the eluent at a flow rate of 0.5 mL/minute while employing a C-18 column (described above). Application of a 1 mg sample of fraction 1 in 250 µl methanol resulted in the separation of the two components or isomeric maltose palmitates. The elution times of the completely resolved components is shown in the following table:

| Component | Elution time (Minutes) | Relative % (by integration of peaks) |
| --- | --- | --- |
| 1 | 16.42 | 31.35 |
| 2 | 20.92 | 68.65 |

FLOW CHART FOR PREPARATION OF MALTOSE PALMITATES

Mixture of palmitoyl chloride and maltose in a 3:1 molar ratio.

1) stir in excess pyridine and dimethyl formamide at 60° for 18 h.
2) evaporate in vacuo to remove solvents Residue 1) dissolve in minimum amount of hot ethanol and pour into cold water
2) filter and dry the resulting precipitate H₂O precipitate filtrate: water, dimethyl formamide and pyridine extract with hot (60°) methanol

| methanol extract: | insoluble residue: maltose penta-hexa, hepta- and octa palmitates |
| --- | --- |

1) cool to 0°
2) filter and dry precipitate

| Methanol Precipitate: maltose mono, di, tri and tetra palmitates | Filtrate: methanol, traces of dimethyl formamide and pyridine |
| --- | --- | extract with heptane: ethanol (95:5)

insoluble residue: maltose monopalmitate heptane: ethanol extract: maltose tetra, tri and di palmitates

| | |
|---|---|
| solvent recovery by distillation | 1) gradient HPLC: heptane:ethanol (95:5) to heptane:ethanol (50:50)<br>2) collect isometrically pure fractions of maltose tetra, tri and dipalmitate<br>3) remove solvent by evaporation in vacuo<br>4) crystallize in 95% ethanol |

Formulation of tetra:tri:di palmitoyl maltose (30:50:20)

METHOD 3

Preparation of anhydrous maltose

It was prepared by dissolving commercial maltose hydrate (Fisher M-75) in pyridine and evaporating the solution under reduced pressure in a vacuum evaporator at 40° C. to achieve azeotropic removal of water of crystallization. Palmitoyl chloride:

It is used as supplied by Aldrich Chem. Co., Cal. N2 P-78.
Procedure of preparation of maltose palmitates:

I. Anhydrous maltose (1 mmole) and palmitoyl chloride (3 mmole) are each dissolved in a small volume of pyridine and the mixture is brought to 80° C. and stirred for 18 hours under a moisture free nitrogen atmosphere. At the end of 18 h, the mixture was subjected to evaporation to remove the pyridine under reduced pressure.

II. The residue was extracted with diethyl ether and then filtered to remove pyridine hydrochloride.

III. The filtrate was evaporated to dryness and the residue was extracted with heptane-ethanol (95:5) and filtered to remove maltose mono palmitate which forms 20 percent of the mixed maltose palmitates (w/w). This procedure provides an easy method for the preparation of maltose monopalmitate.

IV. The heptarte-ethanol extract was re-evaporated and the residue was separated into two fractions using flash chromatography on a silica gel G (Merck 9385) as the solvent. The first fraction (fraction A) was obtained by elution of the column with dichloromethane: MeOH (97:3) ratio. This fraction contains higher homologues of maltose palmitates namely maltose octa, hepta, hexa and penta palmitates. The second fraction (fraction B) was obtained after elution with dichloromethane:MeOH (85:15). It consists of maltose tetra, tri and dipalmitates.

V. Fraction B was evaporated to dryness, then dissolved in heptane:ethanol (50:50) and filtrated through a 0.5 micron membrane in order to remove any dust particles and traces of higher homologous of maltose palmitates. The filtered product is purified by gradient high performance liquid chromatography using a silica gel column and a UV detection system at 214 mm. The solvent gradients system used are heptane: ethanol (95:5) to heptane: ethanol (50:50). Isomerically pure fractions of maltose tetrapalmitate, maltose tripalmitate and maltose dipalmitate, as described previously in method 2, were collected and were simultaneously quantitated using a Waters 730 data module. The fractions were evaporated to dryness in vacuo and trace impurities removed by dissolving in hot 95% ethanol and precipitation by cooling to 0° C. followed by filtration. Under these conditions maltose tripalmitate gives a crystalline product.

Other HPLC techniques that may also be used to purify refined maltose palmitates are tabulated as follows:

| GRADIENT | | ISOCRATIC | | |
|---|---|---|---|---|
| Initial composition | Final composition | Composition | COLUMN | DETECTION |
| Hexane:Ethanol (98:2) | Hexane:Ethanol (50:50) | — | Silica gel | UV 214 or 229 nm |
| Pentane:Methanol (92:2) | Pentane:Methanol (50:50) | — | Silica gel | UV 214 or 229 nm |
| — | — | Chloroform: Methanol 98:.5:.5) | Silica gel | Refractive index |
| Pentane:Methanol (5:95) | Pentane:Methanol (25:75) | — | C-18 | UV 214 or 229 nm |
| Ethanol:Methanol (20:80) | Ethanol (100%) | — | C-18 | UV 214 or 229 nm |
| Isopropanol: Methanol (15:85) | Isopropanol (100%) | — | C-18 | UV 214 or 229 nm |

Characterization of maltose tri and tetrapalmitates

The major peaks eluting in the HPLC employing either of the three methods of HPLC separation were collected and analyzed for glucose to palmitic acid ratio by colorimetric means after acid hydrolysis or maltose: palmitic acid ratio by NMR. Depending on the ratio they were classified as maltose di, tri, tetra etc. palmitates and described as pure or as mixtures based on the ratio and the presence of peaks upon HPLC analysis and thin layer chromatography. Special emphasis was placed on the fractions that gave maltose: palmitic acid ratio of 2.8–3.0 and 3.8 to 4.0. These fractions were rechromatographed and in the case of the first (i.e. maltose tripalmitate) a single peak in the HPLC was obtained. Thus we could isolate pure maltose tripalmitate. Using the same criteria, a double peak with glucose: palmitic acid ratio of 1.95 were isolated and they could be separated into peak 1 and peak 2 when only top of the peak-fractions were collected and the mixed fractions were discarded. These were isomeric maltose tetrapalmitates.

Crystallization of maltose tri and tetra palmitates

The solutions of isomeric maltose tetrapalmitates were evaporated to dryness and then dissolved in a minimum amount of hot 95 percent ethanol. Upon cooling and allowing to stand at 4° C., crystals of the two maltose tetrapalmitates could be obtained. The tubes containing the crystals were centrifuged in the cold and the crystalline products, washed with cold 95 percent ethanol. The early peak maltose tetrapalmitate was referred to as tetra 1 and the later peak as tetra 2.

Tetra 1 had amp of 87°–91° C. and an optical rotation of $[\alpha]_D^{20}=43°$ (C-0.5 in $CHCl_3$). Tetra 2 gave a mp of 105°–107° C. and an optical rotation $[\alpha]_D^{20}=46.44$ (C-0 9 in CHCl₃). Each gave a single band in TLC and a single peak in HPLC. The retention time was 11.6 min for tetra 1 and for the other 11.8 in method 3 of HPLC purification.

The fraction containing maltose tripalmitate was also subjected to dryness in vacuo, redissolved in hot 95 percent ethanol and then left at 4° C. It provided a crystalline product with amp of 159°–162° C. It had a retention time of 13.42 as compared to 11.6–11.8 for maltose tetrapalmitates. Its optical rotation was $[\alpha]_D^{20} = 41°$ ( C-0.5 in CHCl₃).

Structural studies on maltose tri and tetrapalmitates

Same procedures were employed for the characterization of the three products.

1. All three failed to reduce Fehling solution and to reduce silver nitrate showing that the reducing carbon C of maltose was esterified.

2. The products were subjected to periodate oxidation as described by R. G. Spiro in Methods of Enzymology, Vol. 8, pp. 3–52, 1966. Periodate consumption indicated that all three products underwent oxidation. When consumption of periodic acid ceased, excess periodate was exhausted by the addition of ethylene glycol. The reaction mixture was then reduced by sodium borohydride and the reaction mixture subsequently subjected to dilute acid hydrolysis (0.5N HCl for 30 min at 100° C.). The reaction mixture was deionized by mixed resin, evaporated to dryness and subjected to paper chromatography and staining for sugars. Glucose was used as a reference. No spot corresponding to glucose was detected. The result was interpreted to indicate that maltose tri and tetra palmitates contained periodate oxidizable adjacent hydroxyl groups. Since Cl was esterified in the three compounds, and the fact that primary alcoholic group ($CH_2OH$) at C-6 is one of the most reactive groups of glucose for esterification, meant that the C-6 and C-6' of the two glucose residues would be first esterified. That established that maltose tripalmitate is most likely maltose 1, 6, 6' tri palmitate.

Using the same reasoning and the fact that only one maltose tri palmitate was available for further esterification by palmitoyl chloride to form maltose tetrapalmitate with two free adjacent hydroxyls, the choice was limited to the formation of maltose 1, 6, 2', 6' and maltose 1, 6, 4', 6' tetra palmitates. Since these compounds are indistinguishable in NMR and their methylation by diazomethane method results in the release of palmitic acid, it is very difficult to assign to each one of the two specific structures outlined above. The difference in melting point provides insufficient criteria for identification of the structure.

Antitumor activity of maltose tripalmitate and of a formulation of maltose di, tri and tetrapalmitates The scientific and patent literature on tri-fatty acyl disaccharides is non existent. This compound has not been obtained as a single entity. The compound forms complexes and rarely appeared as a pure band in our investigations. However, when the mixture is subjected to HPLC as described in I, we obtain sufficient quantities of di, tri and tetra palmitates. This allowed us to test each of these components individually and in combinations. Briefly, the following results were obtained using C3HBA fragment implanted s.c. in C3H/HeN females.

| Treatment (ip. 3 times weekly) | Day of tumor appearance after implantation | Tumor diameter on day 28 |
| --- | --- | --- |
| PBS | 10–12 | 3'0–3'5 cm |
| 10 µg maltose DiPal | 11–13 | 2'8–3'1 cm |
| 10 µg maltose TriPal | 14–16 | 1'8–2'0 cm |
| 10 µg maltose tetrapalmitate* | 13–14 | 2'1–2'2 cm |
| Formulation of MTP** | | 1'9–2'1 cm |
| (1) 15:35:50 | 13–16 | 2'2–2'3 cm |
| (2) 50:35:15 | 12–13 | 1'8–2'0 cm |
| (3) 25:50:25 | 14–16 | |

*Difficult to deliver since it aggregates and floats in PBS.
**The formulation of MTP consists of maltose dipalmitate: maltose tripalmitate: maltose tetrapalmitate. They form uniform suspensions. One of the major bands which was originally used as MTP contained maltose dipalmitate 10–15 percent, maltose tripalmitate 25 percent, maltose tetrapalmitate 60–65 percent and free palmitic acid about 5 percent which forms a diffused trailing in TLC. Since the ratio of glucose: palmitate was 2 it was thought as pure maltose tetrapalmitate. The formulations were derived by using the antitumor maltose tri and tetrapalmitates and using enough dipalmitate as an emulsifier to obtain fine suspension. A minimum of 10–15 percent dipalmitate is needed.

Preparation of $^3H$ and $^{14}C$ labelled maltose di, tri and tetrapalmitates

Ten mg (0.028 mmole) maltose (Fisher M-75) and 50 µCi $^{14}C$-maltose (ICN 11089) were dissolved in 500 µl pyridine and the solution was evaporated to dryness under reduced pressure in a rotary evaporator at 40° C. The resulting product had a specificity activity of 1786 µCi//mmole. Thirty mg (0.098 mmole) palmitic acid (Aldrich 25,72-5) and 200 µCi 9, 10 $^3H$-palmitic acid (Amersham TRK, 76) and 100 µl thionyl chloride were combined in a conical flask and were heated for one hour at 40° C. Excess thionyl chloride was then removed by evaporating under reduced pressure. The resulting palmitoyl chloride had a specific activity of 1,700 µCi/mmole.

The $^3H$-palmitoyl chloride and the $^{14}C$-maltose (as prepared earlier) were mixed in a total volume of 500 µl of dimethyl formamide (DMF). To the mixture was added 100 µl pyridine and the contents were heated for 14 h at 60° C. in a nitrogen atmosphere. The product was then evaporated under reduced pressure at 60° C. to remove the solvents. It was dissolved in 400 µl of absolute ethanol. Pyridine hydrochloride was removed by adding the dissolved crude reaction product to 1 ml ice cold water in an Eppendorf tube. The resulting suspension was centrifuged at 4° C. for 10 min and the supernatant was discarded. The product was dried for 48 hours in a vacuum desiccator and then was extracted with three 10 µl portions of methanol at room temperature. The methanol extract was subjected to reverse phase HPLC using a methanol eluent and detection at 214 nm at a flow rate of 0.5 ml/min and a 3.9 mn×15 cm Waters Resolve C18 5µ column. Two components eluting at 19.1 and 24.1 min which corresponded to the two isomers of maltose tetrapalmitate were collected. Evaporation of the methanol eluent resulted in the combined recovery of 800 µg maltose tetrapalmitate. Scintillation counting indicated that the product had a specific activity of 1 µCi/mg of $^{14}C$ and 2.6 µCi/mg of $^3H$. The product was dissolved in 90 µl 95% ethanol. Ten µl of $^{14}C$, $^3H$-MTP was administered orally to each of the 8 mice (90,000 cpm/mouse). Two mice were sacrificed at 5, 12, 24 and 48 hours. Tissues from these mice were isolated and frozen, lyophilized and then extracted with CHCl₃:MeOH (2:1). The tissue extracts were analyzed for $^3H$ and $^{14}C$ for non metabolized MTP and its degradation products by scintillation counting.

Metabolism of maltose di, tri and tetra palmitates $^{14}C$-maltose $^3H$ di, tri and tetra palmitates upon oral administration to mice sequestered to different organs and were subsequently degraded. The degradation was evidenced by a change in the $^{14}C/^3H$ ratio of ethanolic extract whereby maltose and palmitic acid released from maltose palmitates were utilized by different routes. $^{14}C$-maltose would degrade to glucose and then transformed to lactic acid, $CO_2$ or other water soluble products whereas $^3H$ fatty acid were stored as fat or other ethanol soluble substances. We did not trace these pathways since they are the accepted routes for glucose and fatty acid utilization. The first tissue to retain high specific concentration of maltose palmitates was the intestine, because of the oral route of administration., However, intestine soon lost maltose palmitates and the highest specific concentration was noted in lymph nodes (inguinal in this case) and in the spleen. Most likely the lymphatic route was used for the circulation of maltose palmitates after absorption in the intestine. These tissues retained maltose palmitates for a longer time since $^{14}C/^3H$ ratio did not decrease rapidly. Other tissues with subsequently sequestered maltose palmitates in a decreasing order were: liver, brain, kidney, lung, heart and skeletal muscle.

The comparative specific distribution of total $^{14}C$ and $^3H$ (total cpm/g tissue) of $^{14}C$-maltose $^3H$tetrapalmitate at 12 h with lymph node taken as 100 were:

Lymph node 100; spleen, 70; liver, 38; brain 35; kidney, 30; lung, 30; heart, 15; skeletal muscle, 5.

The ratio of $^{14}C/^3H$ decreased with time, but the decreases were not similar for different tissues indicating that degrading enzymes were not evenly distributed. The ratio of degradation calculated on the basis of slope of $^{14}C/^3H$ ratio between 24 h and 48 h, in ethanolic extract indicated the following order of degradation, with liver taken as 100:

Liver, 100; kidney, 75; lung, 50; intestine, 50; heart, 40; skeletal muscle, 36; brain, 25; spleen, 20; lymph node, 18.

In a few experiments where only $^3H$-maltose tetrapalmitate was given to 13762 mammary tumor bearing Fisher rats or C3HBA mammary tumor bearing C3H/HeN mice, rapid sequestering and rapid degradation also occurred in the tumor tissue. Degradation also occurred when cultured endothelial cells were incubated with radioactive maltose tri and tetra palmitates, in vitro.

These results indicated that tumor tissue and tumor vasculature were able to remove maltose palmitates from the tumor environment rapidly and this may be the reason that tumor cells soon after implantation were inhibited in their growth by maltose palmitates more severely whereas large size tumors were refractory to their effect. Secondly, the cells of the immune system were less well equipped for maltose palmitate degradation; and hence macrophages and B cells could be activated.

Insofar as the difference between maltose tetra, tri and di palmitate was concerned, maltose tetrapalmitate had higher retention time in tissues, followed by maltose tripalmitate, and maltose dipalmitates were rapidly degraded. Thus in order to provide a continuous supply of maltose tripalmitate, maltose tetrapalmitates are a unique and suitable source. Maltose dipalmitate has emulsifying properties and hence it is a suitable vehicle for providing an emulsion of maltose tetra and triplamitates, but by itself it has poor antitumor activity.

The in vitro growth of an angiosarcoma cell line (Naik-AS) developed by us was studied in the presence and absence of maltose tri- and tetrapalmitates. Both inhibited growth but maltose tripalmitate inhibited growth on the first 30 hours which response declined as it got degraded, whereas maltose tetrapalmitate inhibited little at 30 hours but more at 60 hours as it got degraded to maltoise tripalmitate. These results indicate that tetrapalmitate is the precursor of the most active maltose tripalmitate. As angiosarcomas are endothelial cell tumors, these results also support the anti-angiogenic effect of maltose palmitates. These results are summarized in the following table:

|  | Concentration | % Inhibition of growth of Naik As cells in culture | | |
|---|---|---|---|---|
|  |  | 30 hours | 60 hours | 105 hours |
| Maltose tripalmitate | .625 µg/ml | 25 | 11 | 4 |
|  | 5 µg/ml | 30 | 17 | 10 |
| Maltose tetrapalmitate | .625 µg/ml | 5 | 1 | 0 |
|  | 5 µg/ml | 1 | 30 | 19 |

Based on the results provided by the immune activating effect of maltose palmitates, and their retention and degradation by tissues, we have come to the conclusion that formulation and dose ranges of maltose palmitates should reflect:

a) an absorbable mixture of maltose tetra, tri and dipalmitates; so that maltose dipalmitate constitutes between 15 and 30 percent for emulsification of maltose tri and tetra palmitates. Maltose tripalmitate as an active ingredient should constitute between 25–50 percent whereas maltose tetra palmitate with higher retention time in tissues and as a source of maltose tripalmitate should constitute between 30–60 percent;

b) the concentration used should reflect the degrading ability of the tumor tissue or tissue of origin of the tumor for maltose palmitates; dose for different cancers comparing with lymphomas (which are non degrading) taken as 10 µg/g body weight per day orally should be as follows (in ug/g body weight): brain cancer 15; colon cancer 30; lung cancer 30; kidney cancer 40; liver cancer 50. When breast tumor cells are implanted subcutaneously in rats, the uptake of single-labeled MTP ($^{14}C$ or $^3H$ labelled formulation of di-, tri and tetrapalmitates of maltose) in cancer cells is greater than in liver but lower than in spleen;

c) the frequency of administration should be such as to avoid unnecessary accumulation of the maltose palmitates in normal healthy tissue; we recommend one dose per day orally based on 50 percent clearance per 24 h;

d) if maltose palmitates are being used in combination with angiostatic steroids, their concentration can be reduced (halved) recognizing that angiostatic steroids may be inhibitory to maltose palmitate degradation. Such steroids comprise but are limited to hydrocortisone, 17-β-OH progesterone, cortexolone and tetra hydro S. They were tried at high doses since rodents tolerate them. The doses were: 150 mg/kg of body weight/day for the first two days, 125 mg/kg of body weight/day for the next two days, 100 mg/kg of body weight/day for the next two days, and then a maintenance dose of 75 mg/kg of body weight/day was used for the remaining duration of the treatment, for a total of 20–25 days. In humans, these high doses could be toxic. To our knowledge, only hydrocortisone is approved for human application, and at high doses, it is immunosuppressive. Therefore, the dosage rate of steroids might also be adjusted, according to the patients' response, which is left to the clinician;

e) since genetic make up of mice (mouse strains) differs in their ability to respond immunologically to maltose palmitates, recipients of MTP should be graded with respect to the ability of their lymphocytes to respond immunologically in vitro (e.g. incorporation of $^3H$-thymidine into lymphocytic DNA in the presence and absence of maltose palmitates) and the dose elevated in non or poor responders to obtain a maximal response. It is well known in the case of liposaccharides that non-responder mice (such as C3H/HeJ) will respond to immune effect on dose elevation.

In summary, the present invention provides for a method of obtaining pure homologous series of mono to tetra fatty acyl esters of sugars. A pure homologous series of mono to tetra palmitates of maltose has been obtained in the practice. The flow chart of page 23 can be easily adapted to other fatty acyl esters of other sugars. Examples of other sugars are galactose, glucose, mannose, arabinose, cellobiose and lactose. Fatty acids having a saturated or unsaturated chain length of twelve to twenty carbons are also examples of fatty acids that can be used in the present invention. To be suitable in formulations useful in the treatment of cancer, these other fatty acyl esters of other sugars must be however captured by the target cells, otherwise they can be used for other applications (as detergents or surfactants). Since the present process is based on the separation of mono- to tetra- fatty acyl esters of sugars upon their hydrophobic: hydrophillic balance, it is assumed that these compounds (related to maltose palmitates) can be also obtained in a pure form by following the teachings of the present disclosure, since they have the same or similar hydrophobic: hydrophillic balance as the exemplified mono- to tetrapalmitates of maltose. Therefore, although the present invention has been described hereinabove by way of a preferred embodiment, this embodiment can be modified at will, within the scope of the appended claims, without departing from the spirit and nature of the subject invention.

What is claimed is:

1. A process of production of a pure homologous series of mono-,di-, tri- and tetra- fatty acyl esters of sugar which comprises the following successive steps:

a) mixing a fatty acyl chloride and an anhydrous sugar in a molar ratio of about 3:1 in a first solvent containing pyridine, at a temperature comprised between 60° and 80° C., for about eighteen hours, whereby fatty acyl esters of sugar consisting of a homologous series of mono- to octa- fatty acyl esters of sugars are produced;

b) evaporating said first solvent till the obtention of a dry residue;

c) extracting said dry residue with a second solvent that allows said first solvent to solubilize while said fatty acyl esters of sugar remain in the form of a precipitate, or dissolving said dry residue in hot alcohol and pouring the solution so obtained in a mixture of ice:water, whereby said first solvent solubilize while the fatty acyl esters of sugar precipitate;

the steps a), b) and c) being followed by steps d) to g) or by steps d') to f');

d) extracting said precipitate in a third solvent consisting of a hot alcohol different from and more hydrophillic than the alcohol used in step c), whereby the homologous series of mono- to tetra- fatty acyl esters of sugar solubilize while the homologous series of penta- to octa- fatty acyl esters of sugar remain in the form of a precipitate;

e) separating and cooling the so obtained solution down to 0° C., whereby said third solvent and remaining traces of said first solvent solubilize while the homologous series of mono- to tetra- fatty acyl esters of sugar precipitate;

f) extracting the precipitate so obtained in a fourth solvent of a hydrophilicity such that the homologous series of di- to tetra- fatty acyl esters solubilize while a precipitate consisting of a substantially pure mono- fatty acyl ester of sugar remains in the precipitate in a substantially pure form; and g) fractionating and purifying the so obtained solution, whereby the pure di-, tri- and tetra- fatty acyl esters of sugar are obtained separately;

d') extracting said precipitate in a fifth solvent of a hydrophilicity such that the homologous series of di- to octa- fatty acyl esters of sugar solubilize while the mono-fatty acyl ester of sugar remains in the form of a precipitate, said precipitate being purified till a substantially pure mono- fatty acyl ester of sugar is obtained;

e') submitting the so obtained solution to a fractionation step, first in a sixth solvent of a hydrophilicity such that a first fraction containing the homologous series of penta- to octa- fatty acyl esters of sugar is obtained and second in a seventh solvent of a hydrophilicity such that a second fraction containing the homologous series of di- to tetra- fatty acyl esters of sugar is obtained; and f') submitting said second fraction to a further fractionation step, whereby the di-, tri- and tetra-fatty acyl esters of sugar are obtained in separate fractions, which fractions are further purified to obtain the substantially pure homologous series of di-, tri- and tetra- fatty acyl esters of sugar.

2. A process according to claim 1 wherein said fatty acyl chloride is selected from the group consisting of myristyl, lauryl, palmitoyl, stearyl, oleyl, linolyl and linolenyl chlorides.

3. A process according to claim 1 wherein said sugar is selected from the group consisting of glucose, arabinose, maltose, galactose, mannose, cellobiose and lactose.

4. A process according to claim 2 wherein said fatty acyl chloride is palmitoyl chloride.

5. A process according to claim 3 wherein said sugar is maltose.

6. A process according to claim 1 wherein said fatty acyl esters of sugar are maltose palmitates.

7. A process according to claim 1 wherein said first solvent contains dimethylformamide and pyridine and the temperature is 60° C.

8. A process according to claim 1 wherein said first solvent consists of pyridine and the temperature is 80° C.

9. A process of production of a pure homologous series of mono-, di-, tri- and tetra- palmitates of maltose which comprises the following successive steps:

a) mixing palmitoyl chloride and an anhydrous maltose in a molar ratio of about 3:1 in a first solvent consisting of pyridine, at 80° C., or of a mixture of dimethylformamide and pyridine at 60° C., for eighteen hours, whereby maltose palmitates consisting of a homologous series of mono- to octa- palmitates of maltose are produced;

b) evaporating said first solvent till the obtention of a dry residue;

c) extracting said dry residue with diethyl ether or in a second solvent of similar hydrophilicity that allows said first solvent to solubilize while maltose palmitates remain in the form of a precipitate, or dissolving said dry residue in hot ethanol and pouring the solution so obtained in a mixture of ice:water, whereby said first solvent solubilize while maltose palmitates precipitate;

the steps a), b) and c) being followed by steps d) to g) or by steps d') to f');

d) extracting said precipitate in hot methanol, whereby the homologous series of mono- to tetrapalmitates of maltose solubilize while the homologous series of penta- to octa- palmitates of maltose remain in the form of a precipitate;

e) separating and cooling the so obtained solution down to 0° C., whereby methanol and remaining traces of said first solvent are solubilize while the homologous series of mono- to tetra- palmitates of maltose precipitate;

f) extracting the precipitate so obtained in a fourth solvent consisting of heptane:ethanol 95:5 (v:v) or a solvent of similar hydrophilicity, whereby the homologous series of di- to tetra- palmitates of maltose solubilize while maltose monopalmitate remains in the precipitate in a substantially pure form; and g) fractionating the so obtained solution by high-performance liquid chromatography in a gradient solvent system of heptane:ethanol from 95:5 to 50:50 (v:v) or a gradient solvent system of similar hydrophilicity, whereby separate fractions consisting of di-, tri- and tetra- palmitates of maltose are obtained and further purified till the obtention of pure homologous series of di-, tri- and tetra- palmitates of maltose;

d') extracting said precipitate in a fifth solvent consisting of heptane:ethanol 95:5 (v:v) or a solvent of similar hydrophilicity, whereby the homologous series of di- to octa- palmitates of maltose solubilize while maltose monopalmitate remains in the form of a precipitate, said precipitate being purified till a substantially pure maltose monopalmitate is obtained;

e') submitting the so obtained solution to a fractionation step by flash chromatography in a step gradient solvent system of dichloromethane:methanol from 97:3 to 85:15 (v:v) or a gradient system of similar hydrophilicity, whereby a first fraction containing the homologous series of penta- to octa- palmitates of maltose is obtained and a second fraction containing the homologous series of di- to tetra- palmitates of maltose is obtained; and f') submitting said second fraction to a further fractionation step by high-performance liquid chromatography in a gradient solvent system of heptane:ethanol from 95:5 to 50:50 (v:v) or a gradient solvent system of similar hydrophilicity, whereby separate fractions consisting of di-, tri- and tetrapalmitates of maltose are obtained and further purified till the obtention of pure homologous series of di-, tri- and tetra- palmitates of maltose.

10. A substantially pure homologous series of mono-, di-, tri- and tetra- acyl esters of sugar prepared by the process of claim 1.

11. A substantially pure homologous series of mono-, di-, tri- and tetra- palmitoyl esters of sugar prepared by the process of claim 4.

12. A substantially pure homologous series of mono-, di-, tri- and tetra- palmitates of maltose prepared by the process of claim 6.

13. A substantially pure homologous series of mono-, di-, tri- and tetra- palmitates of maltose prepared by the process of claim 9.

14. A composition for use in the treatment of an angiogenesis-dependent pathology comprising the di-, tri- and tetra-acyl esters of sugar of claim 10.

15. A composition for use in the treatment of an angiogenesis-dependent pathology comprising the di-, tri- and tetra-palmitates of sugar of claim 11.

16. A composition for use in the treatment of an angiogenesis-dependent pathology comprising the di-, tri- and tetra-palmitates of maltose of claim 12.

17. A composition for use in the treatment of an angiogenesis-dependent pathology comprising the di-, tri- and tetra-palmitates of maltose of claim 13.

18. A composition according to claim 16 comprising di-: tri-: tetra- palmitates of maltose in the following respective percentages of weight 15–30: 25–50: 30–60.

19. A composition according to claim 17 comprising di-: tri-: tetra- palmitates of maltose in the following respective percentages of weight 15–30: 25–50: 30–60.

20. A composition according to claim 14 further comprising an angiostatic steroid.

21. A composition according to claim 15 further comprising an angiostatic steroid.

22. A composition according to claim 16 further comprising an angiostatic steroid.

23. A composition according to claim 17 further comprising an angiostatic steroid.

24. A composition according to claim 18 further comprising an angiostatic steroid.

25. A composition according to claim 19 further comprising an angiostatic steroid.

26. A process of production of a pure homologous series of mono-, di-, tri- and tetra- fatty acyl esters of a sugar which comprises the following successive steps:

(a) mixing a fatty acyl chloride and an anhydrous sugar in a molar ratio of about 3:1 in a first solvent containing pyridine, at a temperature between 60° and 80° C., for about eighteen hours, whereby fatty acyl esters of sugar consisting of a homologous series of mono- to octa- fatty acyl esters of sugars are produced;

(b) evaporating said first solvent till the obtention of a dry residue;

(c) extracting said dry residue with a second solvent that allows said first solvent to solubilize while said fatty acyl esters of the sugar remain in the form of a precipitate, or dissolving said dry residue in hot alcohol and pouring the solution so obtained in a mixture of ice:water, whereby said first solvent solubilize while the fatty acyl esters of sugar precipitate;

(d) extracting said, precipitate with a third solvent consisting of a hot alcohol different from and more hydrophillic than the alcohol used in step (c), whereby the homologous series of mono- to tetra- fatty acyl esters of the sugar solubilize while the homologous series of penta- to octa- fatty acyl esters of the sugar remain in the form of a precipitate;

(e) separating and cooling the so obtained solution to 0° C., whereby said third solvent and remaining traces of said first solvent solubilize while the homologous series of mono- to tetra- fatty acyl esters of the sugar precipitate;

(f) extracting the precipitate so obtained in a fourth solvent of a hydrophilicity such that the homologous series of di- to tetra- fatty acyl esters solubilize while a precipitate consisting of a substantially pure monofatty acyl ester of the sugar remains in the precipitate in a substantially pure form; and (g) fractionating and purifying the so obtained solution, whereby the pure di-, tri- and tetra- fatty acyl esters of the sugar are obtained separately.

* * * * *

UNITED STATES PATENT AND TRADEMARK OFFICE
CERTIFICATE OF CORRECTION

PATENT NO. : 5,625,044

DATED : April 29, 1997

INVENTOR(S) : Vijai N. Nigam et al.

It is certified that error appears in the above-identified patent and that said Letters Patent is hereby corrected as shown below:

Title Page, Column 1, field [73], please delete "Goudreau Gage Dubec & Martineau, Montreal" and insert --Université de Sherbrooke, Sherbrooke--.

Signed and Sealed this

Thirtieth Day of March, 1999

Attest:

Attesting Officer

Q. TODD DICKINSON

Acting Commissioner of Patents and Trademarks